United States Patent
Steen et al.

(10) Patent No.: US 7,063,436 B2
(45) Date of Patent: Jun. 20, 2006

(54) LIGHT SOURCE FOR OPHTHALMIC USE

(75) Inventors: Mark E. Steen, Chino Hills, CA (US); Kenneth E. Kadziauskas, Coto de Caza, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 262 days.

(21) Appl. No.: 10/697,060

(22) Filed: Oct. 30, 2003

(65) Prior Publication Data

US 2004/0090796 A1   May 13, 2004

Related U.S. Application Data

(63) Continuation of application No. 10/189,675, filed on Jul. 3, 2002, now Pat. No. 6,786,628.

(51) Int. Cl.
*A61B 18/18* (2006.01)

(52) U.S. Cl. .................... 362/120; 362/109; 606/6

(58) Field of Classification Search ........ 362/554–556, 362/572–575, 109, 119–120, 186; 128/6; 385/117, 902; 606/4, 16, 6; 607/92–93, 607/88; 600/245–249
See application file for complete search history.

(56) References Cited

U.S. PATENT DOCUMENTS

| 6,066,128 | A  | * | 5/2000 | Bahmanyar et al. ........... 606/4 |
| 6,336,904 | B1 | * | 1/2002 | Nikolchev ................... 600/562 |
| 6,423,014 | B1 | * | 7/2002 | Churchill et al. ........... 600/587 |

FOREIGN PATENT DOCUMENTS

JP    2000229090 A  *  8/2000

* cited by examiner

*Primary Examiner*—Alan Cariaso
*Assistant Examiner*—Jason Han
(74) *Attorney, Agent, or Firm*—Advanced Medical Optics, Inc.

(57) ABSTRACT

An instrument for providing illumination of intraocular tissue during surgery generally includes a hand held light source which includes a light emitting diode, a power source for driving the diode and a control switch for interconnecting the diode with the power source. At least one fiber optic having a proximal end in light communication with the LED and a distal end size for insertion into an eye for illumination of intraocular tissue is provided.

3 Claims, 2 Drawing Sheets

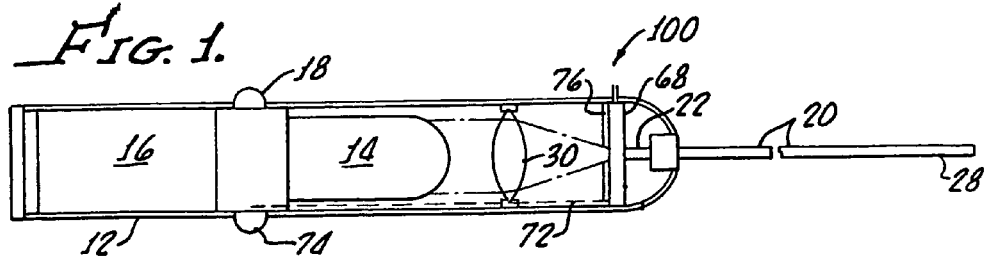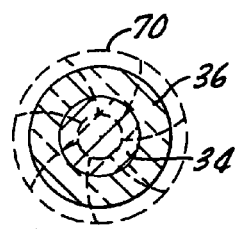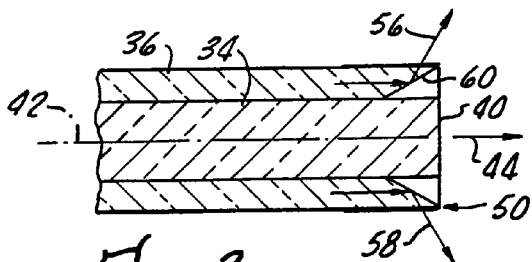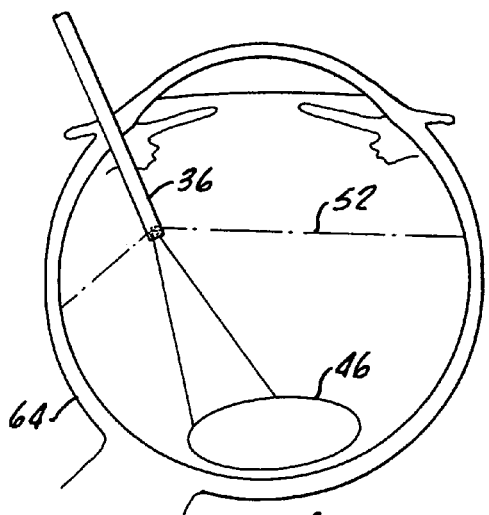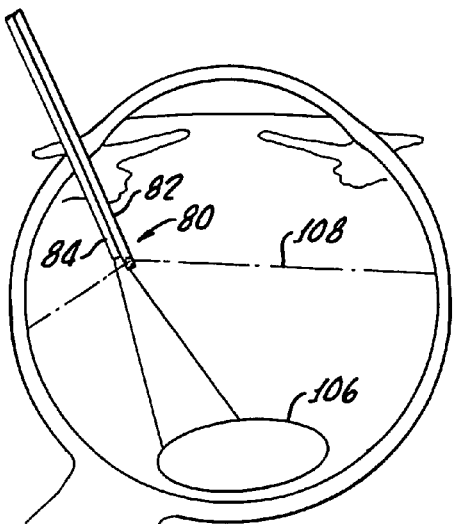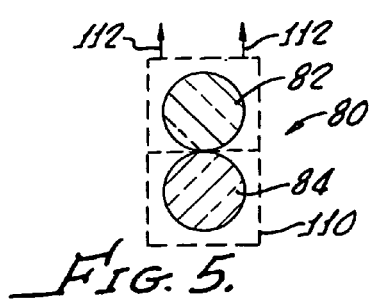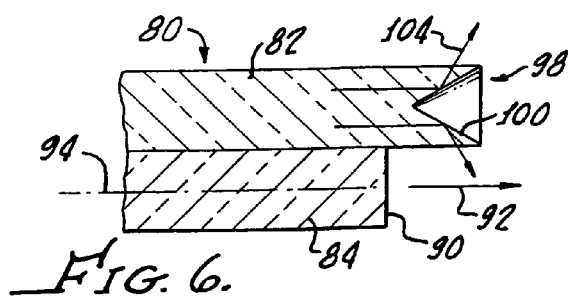

ately difficult to distinguish using conventional
LIGHT SOURCE FOR OPHTHALMIC USE The present application claims priority under 35 U.S.C. §120, and is a Continuation of U.S. application Ser. No. 10/189,675 filed Jul. 3, 2002, now U.S. Pat. No. 6,786,628, which is incorporated by reference herein in its entirety.

Present invention generally relates to the surgical devices and more particularly to devices for illumination of anterior and posterior segments of the eye during surgery. Multiple instruments are typically utilized in performing intraocular surgery which include instruments designed for irrigation, emulsification or cutting in the aspiration tissue.

Sufficient illumination of segments of the eye is difficult with typical microscope lights. Ocular structures such as the cornea, lens and inner ocular fluids are nearly transparent and accordingly difficult to distinguish using conventional illumination due to the small amount of light scatter which they produce when diffusely lit.

Heretofore light pipes have been used to deliver additional illumination of the eye structures during surgery. Typically, a Xenon or Halogen bulb is used to generate light at a surgery console with the resulting light transmitted to the eye via a fiber optic. When using an intense light care must be taken not to damage the retina and accordingly illumination may be focused or directed at an oblique angle and direction away from the retina or sensitive tissue while still providing suitable light to perform the ocular surgery.

Additional problems may be presented in insuring the physician has proper visualization of a surgical device which may be blurred or partially obscured when blood, scar tissue, or other debris is present. Often during phacoemulsification of a cataract in the presence of a small pupil the proximal tip of the surgical device may be obscured.

Depth perception is also dependent upon the amount and type of light present. Heretofore multiple light sources have been used interchangeably in order to provide appropriate illumination. This of course requires repeated insertion and removal of instruments. Alternatively, multiple surgical openings in the eye and multiple illuminators may be used, however this adds to the risk of complications and may increase the difficulty of the surgical procedure.

The present invention is directed to a hand held device which can be utilized to provide either a focused or indirect beam of light, which is hereinafter referred to as chandelier, or floodlight, type illumination, or both as desired.

SUMMARY OF THE INVENTION

An instrument in accordance with the present invention for providing illumination of intraocular tissue during surgery generally includes a hand held light source with a light source comprising a light emitting diode (LED), a power source for driving the LED and a control switch for interconnecting the LED with the power source.

At least one fiber optic having a proximal end in light communication with the LED and a distal end size for insertion into an eye for illumination of intraocular tissue is provided.

More particularly the instrument accordance with the present invention may include two fiber optics. A first of the two fiber optics may have a distal end for directing light along a longitudinal axis of the first fiber optic and a second of the two fiber optics may have a distal end for emitting light in a chandelier, or floodlight fashion.

In one embodiment of the present invention first and second fiber optics are co-axial and in a second embodiment the fiber optics may be parallel.

A light director may be disposed in a hand held light source for enabling light passage into one or both of the first and second fiber optics.

A shutter may be provided for control of the passage of light into the first and second light fiber optics. In one embodiment the shutter may be an iris, and in another embodiment the shutter may be a plane shutter. A mechanical linkage may be provided for enabling manual control of the light transmitted through the fiber optics.

In addition, a color filter may be provided in order to enhance visual perception of eye tissue.

In an alternative embodiment of the present invention the LED is disposed at a distal end of a needle and a needle lumen enables electrical connection between the LED and the power source

BRIEF DESCRIPTION OF THE DRAWINGS

A better understanding of the present invention maybe realized from consideration of the following detailed description when taken in conjunction with the accompanying drawings in which:

FIG. 1 is a side view representation of the instrument in accordance with the present invention generally showing a light emitting diode (LED) a power source and a control switch along with at least one fiber optic having a proximal end in light communication with the LED and the distal end size for insertion into an eye or illumination of intraocular tissue;

FIG. 2 is a cross sectional view of one embodiment of the present invention utilizing two co-axial optical fibers and showing in dashed line an iris type shutter for controlling light thereunto;

FIG. 3 is a cross sectional view of the fiber optics shown in FIG. 2 illustrating both directed illumination and diffuse, or chandelier type illumination;

FIG. 4 is a representation showing illumination available from the fiber optics shown in FIGS. 2 and 3;

FIG. 5 is a cross sectional view of an alternative embodiment in accordance with the present invention utilizing two parallel fiber optics;

FIG. 6 is a cross sectional view of the co-axial fiber optics shown in FIG. 5;

FIG. 7 is a diagram illustrating the use of the fiber optics shown in FIGS. 5 and 6 to illuminate intraocular tissue;

DETAILED DESCRIPTION

Figure 8:
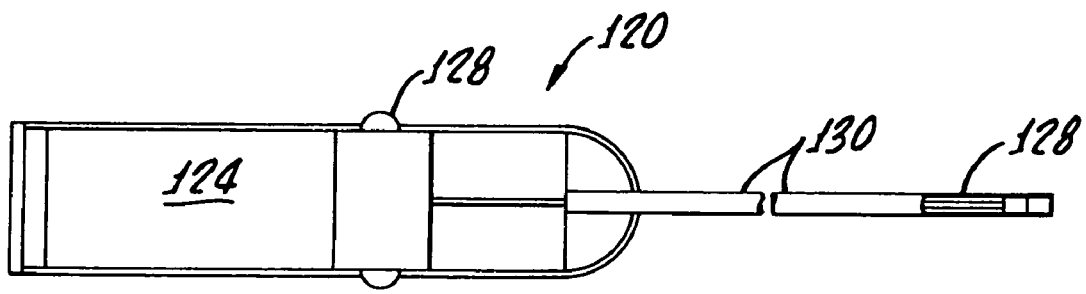
FIG. 8 is a side view representation of an alternative embodiment of the present invention in which an LED is disposed at a distal end of a needle.
Figure 9:
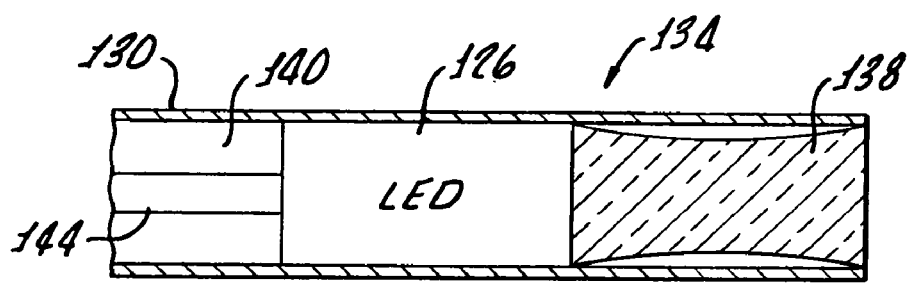
FIG. 9 is an enlarged view of the needle distal end shown in FIG. 8 more clearly showing a lens for focusing light emitted from the LED.

With reference to FIG. 1 there is shown an instrument 10 in accordance with the present invention for providing illumination of intraocular tissue (not shown) during surgery. A housing 12 incases a light source 14, preferably an LED, a battery power source 16 and a control switch 18 for interconnecting the LED 14 with the power source.

As hereinafter discussed in greater detail, at least one fiber optic 20 is provided with a proximal end 22 in light communication with the LED and a distal end 28 sized for insertion into an eye (not shown) for illumination of intraocular tissue (not shown). A lens and/or filter 30 may be used to focus light onto the fiber optic proximal end 22 or direct coupling may be utilized. In addition a shutter arrangement 68 may be utilized for controlling light passage into the fiber optic 20. Thus in accordance with the present invention the LED is utilized instead of the standard Xenon or Halogen bulb in a console (not shown) to provide illumination without a high level of heat generated and with a significantly lower level of power. It should be appreciated that the hand held device 10 may be constructed at low cost and be disposable or of limited reuse.

One embodiment the instrument 10, in accordance with the present invention, may incorporate two co-axial fibers 34, 36. The first fiber 34 includes a distal end 40, as shown in FIG. 3, for directing light along a longitudinal axis 42 as shown by the arrow 44 this results in spot illumination as indicated by the pattern 46 shown in FIG. 4.

The second fiber 36 includes a distal end 50 for directing light in a chandelier, or floodlight fashion as shown by the dashed line 52 in FIG. 4. This illumination is indicated by the arrows 56, 58 in FIG. 3 may be achieved by providing an angled surface 60. The angular relationship of the surface 60 may be utilized to direct the light, as represent by the arrows 56, 58 in up to a 180 degree pattern about the longitudinal axis 42 with the light being emitted at angles of up to 90 degrees from the longitudinal axis 42 or more if desired.

This emission is a chandelier lighting effect within the eye 64, is represented in FIG. 4.

In order to control light emission from the fiber optic distal ends 40, 50 a shutter 68, as represented in FIG. 1, maybe utilized.

More specifically with regard to the embodiment shown in FIG. 2 the shutter maybe in the form of an iris type shutter 70 shown in dashed line in FIG. 2 and conventionally controlled by way of a linkage 72 shown in dashed line in FIG. 1 through a controller 74. Thus the shutter 68 acts as a director which is disposed in the hand held light source for enabling light passage into one of the first and second fiber optics 34, 36.

In addition, a color filter 76 may be disposed between the light source 14 and fiber optic end 22 for controlling a light spectrum passing into the fiber optic 20. Selected color filters, such as, for example green, may be used to highlight red tissue.

A second embodiment of fiber optics 80 is shown in FIGS. 5 and 6. A first and second fiber optic 82, 84 are disposed in a parallel arrangement with the first fiber optic 84 having a distal end 90 for emitting light as indicated by the arrow 92 along a longitudinal axis 94 of the fiber 84.

The second fiber 82 includes a distal end 98 including a surface 100 thereon for emitting light in a chandelier fashion as indicated by the arrow 104 and as hereinabove described in connection with FIG. 3. FIG. 7 illustrates the illumination patterns which are similar to that shown in FIG. 4. Specifically, the fiber 84 enables a directed pattern 106 of light while the fiber 82 provides for a chandelier, or flood light type of illumination as indicated by the dashed line 108.

Control of light entry into the fibers 82, 84 is by way of a plane shutter 110 which is moveable in the direction of arrows 112 for directing light from the LED 14 into one or both of the fibers 82, 84 as desired. The shutter 110 may be of conventional design.

An alternative embodiment of the present invention is shown in FIG. 8 and includes a hand held light source 120 including a power source 124, a light emitting diode (LED) 126 and a control switch 128.

A needle 130, preferably 20 gauge or less, is provided with a distal end 134 for supporting the LED 126 along with a lens 138. Light introduced into the lens 138 from the abutting LED 126 is focused, with the focusing being controlled by an hourglass shape of the lens 138.

A lumen 140 enables communication between the LED 126 and the power source 124 with an electrical connection 144.

Although there has been hereinabove described various specific arrangements of an instrument for providing illumination of intraocular tissue during surgery for the purpose of illustrating a manner in which the invention maybe used to advantage, it will be appreciated that the invention is not limited thereto. Accordingly, any and all modifications come with variations or equivalent arrangements which may occur to those skilled in the arts should be considered to be within the scope of the invention as defined in the appended claims.

What is claimed is:

1. An instrument for providing illumination of intraocular tissue during surgery, said instrument comprising:
   a hand held light source, the light source comprising:
      a housing;
      at least one light emitting diode (LED), a power source for driving the LED and a control switch for interconnecting the LED with said power source, wherein the power source is disposed within the housing; and
      at least one needle for insertion into an eye and for supporting the LED at a distal end of the needle, the needle including a lumen for communicating an electrical connection between the LED and said power source, said power source being disposed at a proximal end of said housing.

2. The instrument according to claim 1, further comprising a lens disposed at the distal end of the needle for focusing light emitted from said LED.

3. The instrument according to claim 2, wherein said lens has an hourglass shape.

* * * * *